(12) United States Patent
Donovan et al.

(10) Patent No.: US 9,545,281 B2
(45) Date of Patent: Jan. 17, 2017

(54) MINIMALLY INVASIVE CEMENT DELIVERY SYSTEM RETAINER

(71) Applicant: Kyphon SARL, Neuchatel (CH)

(72) Inventors: Brian W. Donovan, San Jose, CA (US); Andrea Y. Leung, Milpitas, CA (US); Bryan A. Click, Fremont, CA (US)

(73) Assignee: KYPHON SARL, Neuchatel (CH)

( * ) Notice: Subject to any disclaimer, the term of this patent is extended or adjusted under 35 U.S.C. 154(b) by 196 days.

(21) Appl. No.: 14/316,299

(22) Filed: Jun. 26, 2014

(65) Prior Publication Data
US 2014/0309647 A1    Oct. 16, 2014

Related U.S. Application Data

(62) Division of application No. 12/430,047, filed on Apr. 24, 2009, now Pat. No. 8,821,505.

(51) Int. Cl.
| | |
|---|---|
| *A61B 17/88* | (2006.01) |
| *A61B 17/56* | (2006.01) |
| *A61B 17/00* | (2006.01) |

(52) U.S. Cl.
CPC ....... *A61B 17/8811* (2013.01); *A61B 17/8816* (2013.01); *A61B 17/8822* (2013.01); *A61B 17/8855* (2013.01); *A61B 2017/00539* (2013.01)

(58) Field of Classification Search
CPC ............ A61B 17/8855; A61B 17/8822; A61B 17/8816; A61B 17/8811; A61B 2017/00539
See application file for complete search history.

(56) References Cited

U.S. PATENT DOCUMENTS

| | | | | |
|---|---|---|---|---|
| 3,726,522 A | * | 4/1973 | Silberman | A63B 21/0728 285/322 |
| 4,149,535 A | * | 4/1979 | Volder | A61M 5/1582 604/164.01 |
| 4,752,292 A | * | 6/1988 | Lopez | A61M 39/1011 604/244 |
| 4,838,282 A | | 6/1989 | Strasser et al. | |
| 4,960,412 A | * | 10/1990 | Fink | A61M 39/0606 604/167.04 |
| 5,147,316 A | * | 9/1992 | Castillenti | A61B 17/34 604/164.04 |
| 5,195,964 A | * | 3/1993 | Kletzky | A61B 17/42 604/264 |
| 5,217,441 A | * | 6/1993 | Shichman | A61B 17/3403 604/164.01 |
| 5,312,351 A | * | 5/1994 | Gerrone | A61B 17/3417 604/117 |

(Continued)

*Primary Examiner* — Zade Coley
(74) *Attorney, Agent, or Firm* — Sorell Lenna & Schmidt LLP

(57) ABSTRACT

A system for performing a minimally invasive surgical procedure comprises a cannula, a bone filler material delivery nozzle for performing the procedure through the cannula, and a retainer for securing the delivery nozzle relative to the cannula. The retainer eliminates the need to manually stabilize and position the delivery nozzle during the procedure, thereby allowing the physician to perform the procedure outside of the fluoroscopic radiation field used to visualize the procedure location. The retainer can be attached to the cannula, and can provide either selective or constant clamping force onto the delivery nozzle.

19 Claims, 12 Drawing Sheets

(56) References Cited

U.S. PATENT DOCUMENTS

| | | | | |
|---|---|---|---|---|
| 5,320,608 | A * | 6/1994 | Gerrone | A61B 17/3417 604/117 |
| 5,468,228 | A * | 11/1995 | Gebert | A61M 25/02 128/DIG. 26 |
| 5,800,451 | A * | 9/1998 | Buess | A61B 17/3421 604/167.03 |
| 6,214,012 | B1 * | 4/2001 | Karpman | A61B 17/864 606/246 |
| 6,217,568 | B1 * | 4/2001 | Jepson | A61J 1/2089 604/167.02 |
| 6,241,734 | B1 * | 6/2001 | Scribner | A61B 17/8816 606/93 |
| 6,261,282 | B1 * | 7/2001 | Jepson | A61M 39/045 128/912 |
| 6,355,028 | B2 * | 3/2002 | Castaneda | A61B 17/3417 600/201 |
| 6,488,667 | B1 | 12/2002 | Murphy | |
| 6,540,738 | B2 * | 4/2003 | Kurfess | A61B 17/3415 600/114 |
| 6,582,420 | B2 * | 6/2003 | Castaneda | A61B 17/3417 604/164.04 |
| 6,582,446 | B1 * | 6/2003 | Marchosky | A61B 17/8822 606/167 |
| 6,749,589 | B1 * | 6/2004 | Douglas | A61M 25/0097 604/162 |
| 7,086,560 | B2 * | 8/2006 | Shioya | G07F 11/32 221/191 |
| 7,112,205 | B2 * | 9/2006 | Carrison | A61B 17/3472 606/92 |
| 7,175,336 | B2 * | 2/2007 | Voellmicke | A61F 2/4644 366/160.4 |
| 7,297,138 | B2 * | 11/2007 | Fangrow, Jr. | A61M 5/158 604/164.01 |
| 7,628,774 | B2 * | 12/2009 | Fangrow, Jr. | A61M 39/02 251/149.1 |
| 7,717,947 | B1 * | 5/2010 | Wilberg | A61B 17/864 606/304 |
| 8,382,808 | B2 * | 2/2013 | Wilberg | A61B 17/7098 411/82.1 |
| 2004/0092946 | A1 * | 5/2004 | Bagga | A61B 17/16 606/93 |
| 2004/0122438 | A1 * | 6/2004 | Abrams | A61B 17/8816 606/93 |
| 2006/0052794 | A1 * | 3/2006 | McGill | A61B 17/8816 606/93 |
| 2007/0032794 | A1 * | 2/2007 | Weber | A61B 17/1604 606/92 |
| 2007/0197971 | A1 * | 8/2007 | Krueger | A61B 17/8819 604/164.01 |
| 2007/0198024 | A1 * | 8/2007 | Plishka | A61B 17/8811 606/93 |
| 2009/0054934 | A1 * | 2/2009 | Beyar | A61L 24/001 606/86 R |
| 2010/0036381 | A1 * | 2/2010 | Vanleeuwen | A61B 17/1617 606/80 |
| 2010/0160921 | A1 * | 6/2010 | Sun | A61B 17/885 606/92 |

* cited by examiner

MINIMALLY INVASIVE CEMENT DELIVERY SYSTEM RETAINER

CROSS-REFERENCE TO RELATED APPLICATIONS

This application is a division of application Ser. No. 12/430,047, filed on Apr. 24, 2009, the contents of which are herein incorporated by reference in their entirety.

FIELD OF THE INVENTION

The invention relates to a system and method for performing a surgical procedure, and in particular, to a minimally invasive surgical system that includes a restraining mechanism to ensure positional stability of a bone filler device without requiring manual support of that device.

BACKGROUND OF THE INVENTION

A minimally invasive procedure is a medical procedure that is performed through the skin or an anatomical opening. In contrast to an open procedure for the same purpose, a minimally invasive procedure will generally be less traumatic to the patient and result in a shortened recovery period.

However, there are numerous challenges that minimally invasive procedures present. For example, minimally invasive procedures are typically more time-consuming than their open procedure analogues due to the challenges of working within a constrained operative pathway. In addition, as minimally invasive procedures have evolved, unique challenges have arisen that require new solutions.

For example, for many individuals in our aging world population, undiagnosed and/or untreatable bone strength losses have weakened these individuals' bones to a point that even normal daily activities pose a significant threat of fracture. In one common scenario, when the bones of the spine are sufficiently weakened, the compressive forces in the spine can cause fracture and/or deformation of the vertebral bodies. For sufficiently weakened bone, even normal daily activities like walking down steps or carrying groceries can cause a collapse of one or more spinal bones. A fracture of the vertebral body in this manner is typically referred to as a vertebral compression fracture. Other commonly occurring fractures resulting from weakened bones can include hip, wrist, knee and ankle fractures, to name a few.

Fractures such as vertebral compression fractures often result in episodes of pain that are chronic and intense. Aside from the pain caused by the fracture itself, the involvement of the spinal column can result in pinched and/or damaged nerves, causing paralysis, loss of function, and intense pain which radiates throughout the patient's body. Even where nerves are not affected, however, the intense pain associated with all types of fractures is debilitating, resulting in a great deal of stress, impaired mobility and other long-term consequences. For example, progressive spinal fractures can, over time, cause serious deformation of the spine ("kyphosis"), giving an individual a hunched-back appearance, and can also result in significantly reduced lung capacity and increased mortality.

Until recently, treatment options for vertebral compression fractures, as well as other serious fractures and/or losses in bone strength, were extremely limited—mainly pain management with strong oral or intravenous medications, reduced activity, bracing and/or radiation therapy, all with mediocre results. Because patients with these problems are typically older, and often suffer from various other significant health complications, many of these individuals are unable to tolerate invasive surgery. In addition, to curb further loss of bone strength, many patients are given hormones and/or vitamin/mineral supplements—again with mediocre results and often with significant side effects.

In an effort to more effectively and directly treat vertebral compression fractures, minimally invasive techniques such as vertebroplasty and, subsequently, kyphoplasty, have been developed. Vertebroplasty involves the injection of a flowable reinforcing material, usually polymethylmethacrylate (PMMA—commonly known as bone cement), into a fractured, weakened, or diseased vertebral body. Shortly after injection, the liquid filling material hardens or polymerizes, beneficially supporting the vertebral body internally, alleviating pain and preventing further collapse of the injected vertebral body.

Because the liquid bone cement naturally follows the path of least resistance within bone, and because the small-diameter needles used to deliver bone cement in vertebroplasty procedure require either high delivery pressures and/or less viscous bone cements, ensuring that the bone cement remains within the already compromised vertebral body is a significant concern in vertebroplasty procedures. Kyphoplasty addresses this issue by first creating a cavity within the vertebral body (e.g., with an inflatable balloon) and then filling that cavity with bone filler material. The cavity provides a natural containment region that minimizes the risk of bone filler material escape from the vertebral body. An additional benefit of kyphoplasty is that the creation of the cavity can also restore the original height of the vertebral body, further enhancing the benefit of the procedure.

In both vertebroplasty and kyphoplasty, as with most minimally invasive procedures, x-ray fluoroscopy is used to allow the surgeon to visualize the procedural actions being performed within the patient. Unfortunately, efforts to move the physician out of the fluoroscopic field are often hampered by the nature of traditional minimally invasive instruments. Specifically, the devices used to deliver bone filler material during minimally invasive procedures have typically been designed to be manipulated and held from just outside the working cannula (or plunged directly into the vertebral body without the use of a cannula). Therefore, adding remote operation capabilities (e.g., via flexible tubing or hydraulic lines) can be difficult due to the tendencies of the tubing or other connection/control lines to cause unintended movement of the instrument within the working cannula.

Accordingly, it is desirable to provide surgical tools and techniques that enable the stable and secure operation of a bone filler material delivery device through a cannula.

SUMMARY OF THE INVENTION

By providing a releasable retainer for coupling a bone filler material delivery nozzle and a working cannula, a minimally invasive surgical procedure can be performed from outside the fluoroscopic radiation field used for visualization. The retainer ensures that the delivery nozzle remains properly positioned with respect to the cannula during the procedure, yet allows simple disengagement/removal of the delivery nozzle to minimize procedure duration.

In one embodiment, a minimally invasive surgical system or kit can include a cannula, a bone filler material delivery nozzle for use in a minimally invasive surgical procedure (e.g., kyphoplasty) through the cannula, and a retainer. In various embodiments, the system can include additional tools and instructions for use that specify how the system is to be used. The retainer attaches to the cannula and maintains the position of the delivery nozzle relative to the cannula during the surgical procedure. Because the cannula is typically firmly anchored in the patient (e.g., within cortical bone) during the procedure, the retainer ensures that the delivery nozzle remains properly positioned as well.

In one embodiment, the retainer can comprise a gripping mechanism that exerts a constant gripping force on the delivery nozzle once it is placed within the cannula. In various embodiments, the gripping mechanism can include o-rings, gaskets, flexible arms or linkages, or any other mechanism that can provide a gripping force sufficient to hold the delivery nozzle in place during the surgical procedure. Once the procedure is complete, the delivery nozzle can be pulled from the gripping mechanism. In one embodiment, the delivery nozzle can include mating features (e.g., detents) that positively mate with the gripping mechanism and thereby define one or more distinct positions for the delivery nozzle relative to the cannula.

In various other embodiments, the retainer can comprise a gripping mechanism that only exerts a gripping force on the delivery nozzle when a clamping mechanism is actuated. In one embodiment, the gripping mechanism can include multiple arms having a default spacing that allows the delivery nozzle to pass through freely, and a clamping element that selectably forces the arms together to grip the delivery nozzle. In one embodiment, the clamping element is a cap that threads over the arms and includes an internal taper that forces the arms together as the cap is tightened down.

In one embodiment, the retainer includes a latching mechanism to connect to the cannula. In various other embodiments, the connection between the retainer and the cannula can include one or more clips, pins, hooks, snaps, magnets, or any other mechanism or combination of mechanisms for temporarily securing the retainer to the cannula.

In another embodiment, a method for performing a minimally invasive surgical procedure includes placing a cannula in a patient, attaching a retainer to the cannula, placing a delivery nozzle in the cannula, securing the delivery nozzle relative to the cannula using the retainer, and performing the procedure using the delivery nozzle. In one embodiment, securing the delivery nozzle relative to the cannula includes placing the cannula in the retainer and moving the delivery nozzle through the retainer until a desired position is achieved, wherein the retainer applies a constant gripping force to the delivery nozzle as it is moved through the retainer.

In another embodiment, securing the delivery nozzle relative to the cannula involves placing the cannula in the retainer, and then applying a clamping force to the retainer to cause the retainer to grip the delivery nozzle. In one embodiment, applying the clamping force includes threading a cap with an internal taper over multiple arms that surround the delivery nozzle, such that the internal taper forces the multiple arms inward and into contact with the delivery nozzle.

In one embodiment, delivering bone filler material can include remotely causing the bone filler material to be dispensed from the delivery nozzle into bone (e.g., via hydraulic pressure or material delivery via flexible tubing) as part of a kyphoplasty or vertebroplasty procedure.

As will be realized by those of skilled in the art, many different embodiments of an introducer/guide pin device, systems, kits, and/or methods of using an introducer/guide pin device according to the present invention are possible. Additional uses, advantages, and features of the invention are set forth in the illustrative embodiments discussed in the detailed description herein and will become more apparent to those skilled in the art upon examination of the following.

DETAILED DESCRIPTION

By providing a releasable retainer for coupling a bone filler material delivery nozzle and a working cannula, a minimally invasive surgical procedure can be performed from outside the fluoroscopic radiation field used for visualization. The retainer ensures that the delivery nozzle remains properly positioned with respect to the cannula during the procedure, yet allows simple disengagement/removal of the delivery nozzle to minimize procedure duration.

Figure 1:
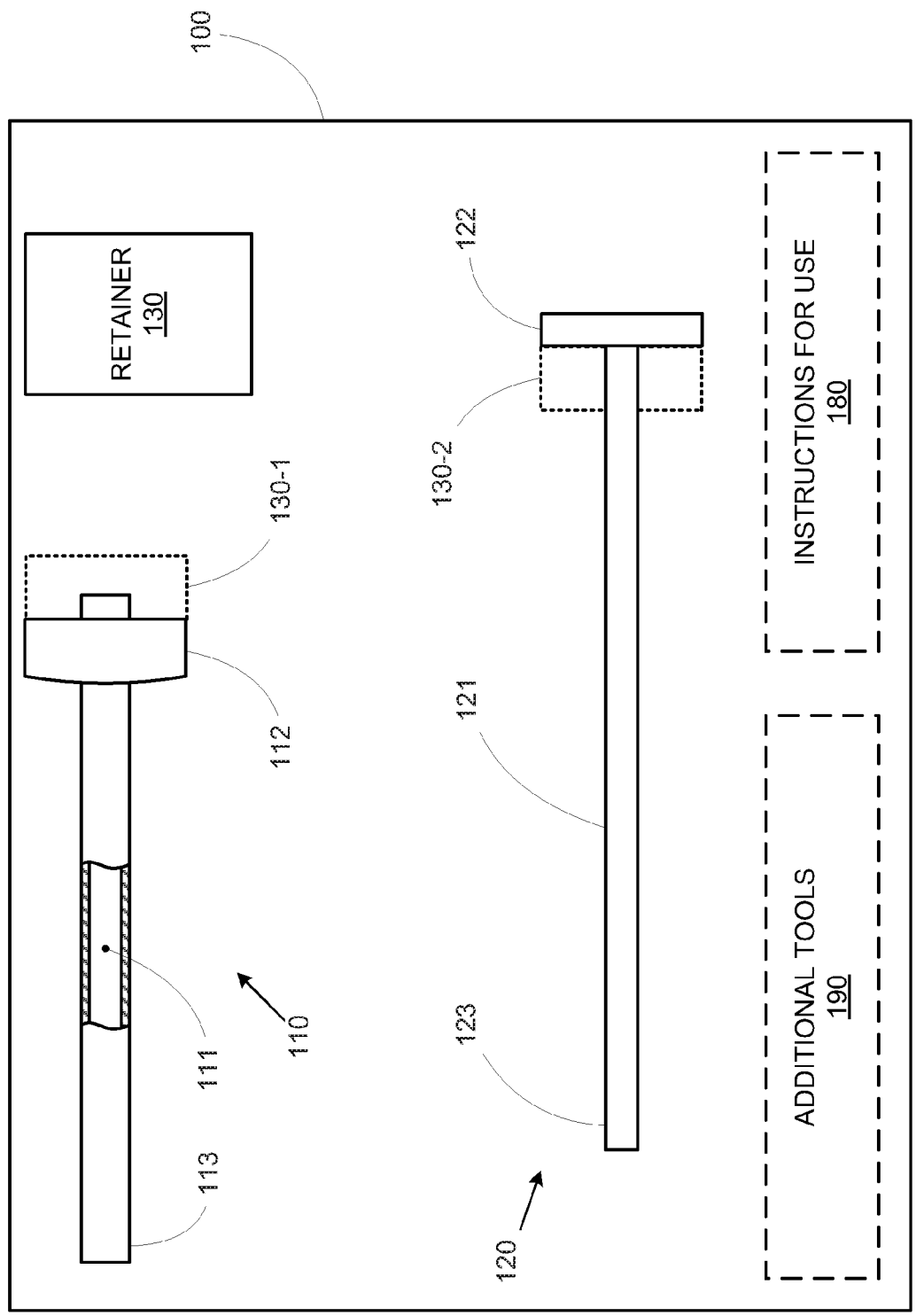
FIG. 1 is a minimally invasive surgical system that includes a cannula, a bone filler material delivery nozzle, and a retainer for selectively securing the delivery nozzle to the cannula.

FIG. 1 shows a system 100 for use in a minimally invasive surgical procedure. System 100 includes a cannula 110, a bone filler material delivery nozzle 120 sized to fit through a lumen 111 of cannula 110, and a retainer 130 for securing delivery nozzle 120 with respect to cannula 110 during the surgical procedure. In various embodiments, system 100 can be a kit providing a prepackaged collection of items for performing the surgical procedure, including optional instructions for use 180 for describing the proper application of system 100, and optional additional tools 190.

In various embodiments, retainer 130 can be a discrete element that attaches to a proximal end 112 of cannula 110 during the surgical procedure, and can be used to hold or clamp delivery nozzle 120 while delivery nozzle 120 is positioned within lumen 111 of cannula 110. Note that in various other embodiments, retainer 130 can be integrated with cannula 110 (e.g., optional retainer 130-1) or can be integrated with delivery nozzle 120 (e.g., optional retainer 130-2).

Figure 4A:
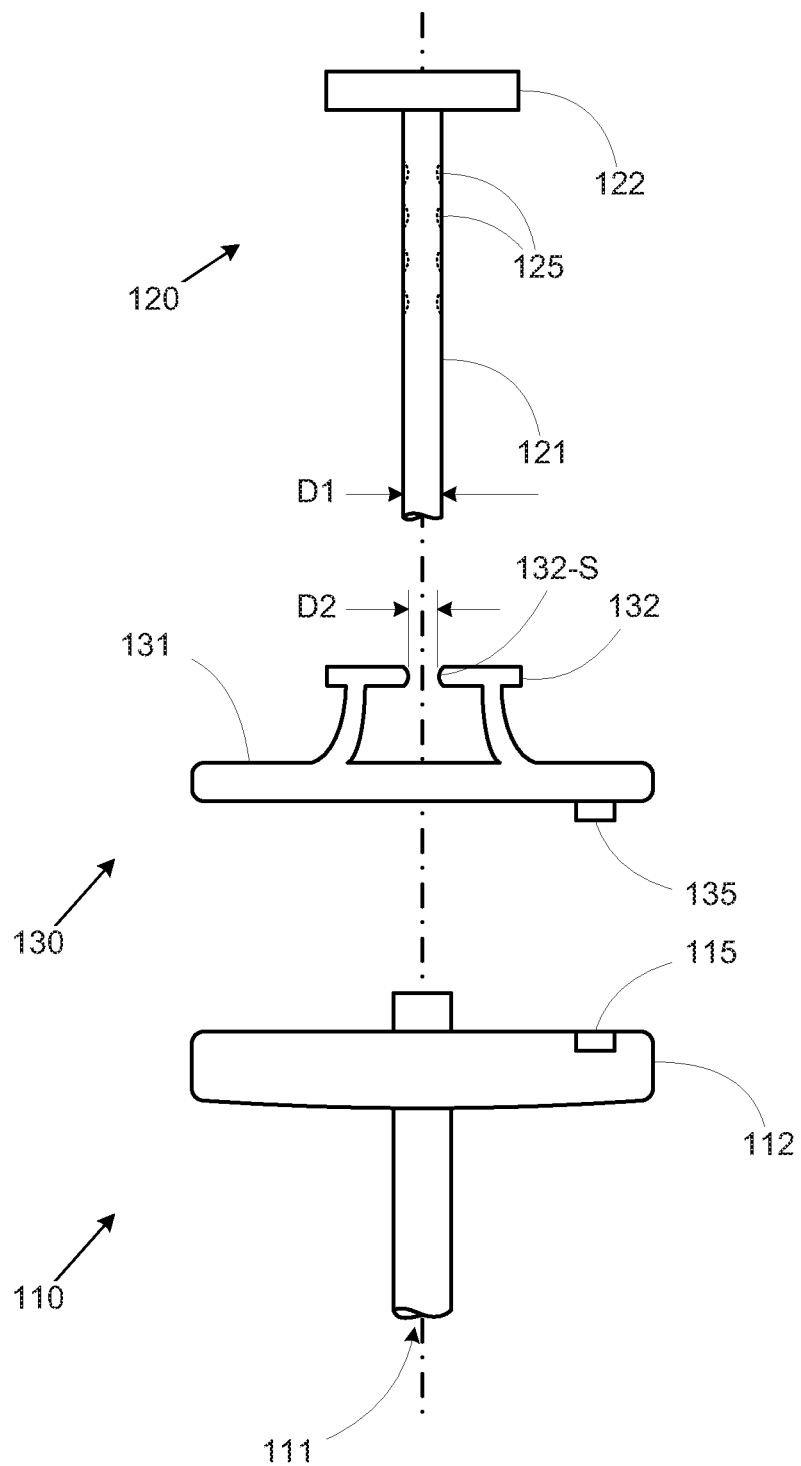
FIGS. 4A-4D show exemplary embodiments of the retainer of FIG. 1.

Retainer 130 can include any type of mechanism that can secure delivery nozzle 120 and prevent unwanted motion relative to cannula 110 during the surgical procedure. For example, FIG. 4A shows an exemplary retainer 130 that includes a base structure 131 having (or coupled to) gripping arms 132 with gripping surfaces 132-S that are spaced by a default spacing D2 (i.e., normal spacing, when not in contact with the delivery nozzle) that is less than a dimension D2 at a gripping region of delivery nozzle 120. Retainer 130 further includes a securing element 135, such as a latch, clip, pin, hook, snap, magnet, or any other mechanism that can secure retainer 130 to cannula 110 via a mating securing element 115.

Figure 4B:
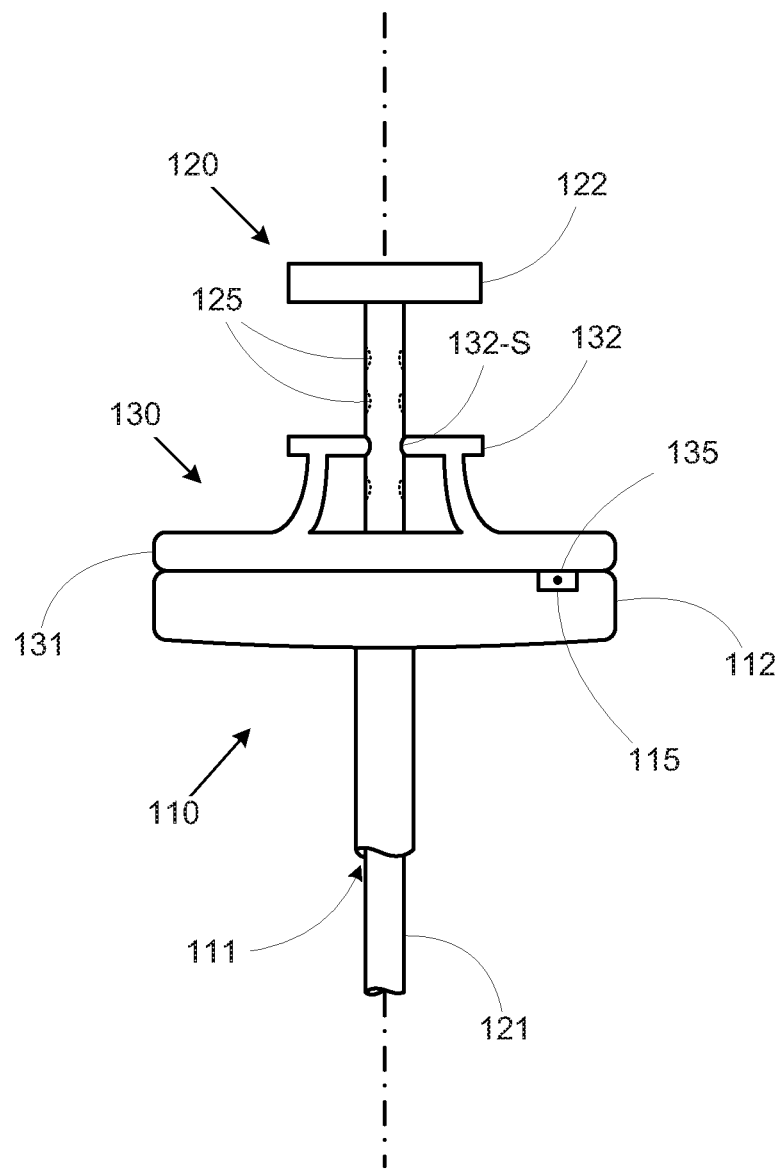

Therefore, when securing elements 135 and 115 are engaged, as shown in FIG. 4B, retainer 130 is fixedly coupled to cannula 110. When delivery nozzle 120 is placed into cannula 110 past retainer 130, gripping arms 132 press gripping surfaces 132-S against the sides of a section of delivery nozzle 120 (in this case, shaft 121) to hold delivery nozzle 120 in place relative to cannula 110. In one embodiment, delivery nozzle 120 can include optional features 125 (e.g., detents, grooves, ridges, bumps, indentations, or other features) that positively mate with gripping surfaces 132-S (i.e., interlock or fit together) to provide one or more discrete positions for delivery nozzle 120 relative to cannula 110.

In various other embodiments, gripping arms 132 can be articulating arms that are biased inward (i.e., towards the centerline of retainer 130), thereby providing a natural clamping effect to hold delivery nozzle 120. The articulation can be provided by material flexibility, spring loading, or any other mechanism. In other embodiments, gripping arms 132 can be substantially rigid, but gripping surfaces 132-S can include a resilient or compressible element (e.g., an elastomer, an o-ring, a gasket, or a spring-loaded tip) that provides an elastic or frictional gripping force on delivery nozzle 120.

Figure 4C:
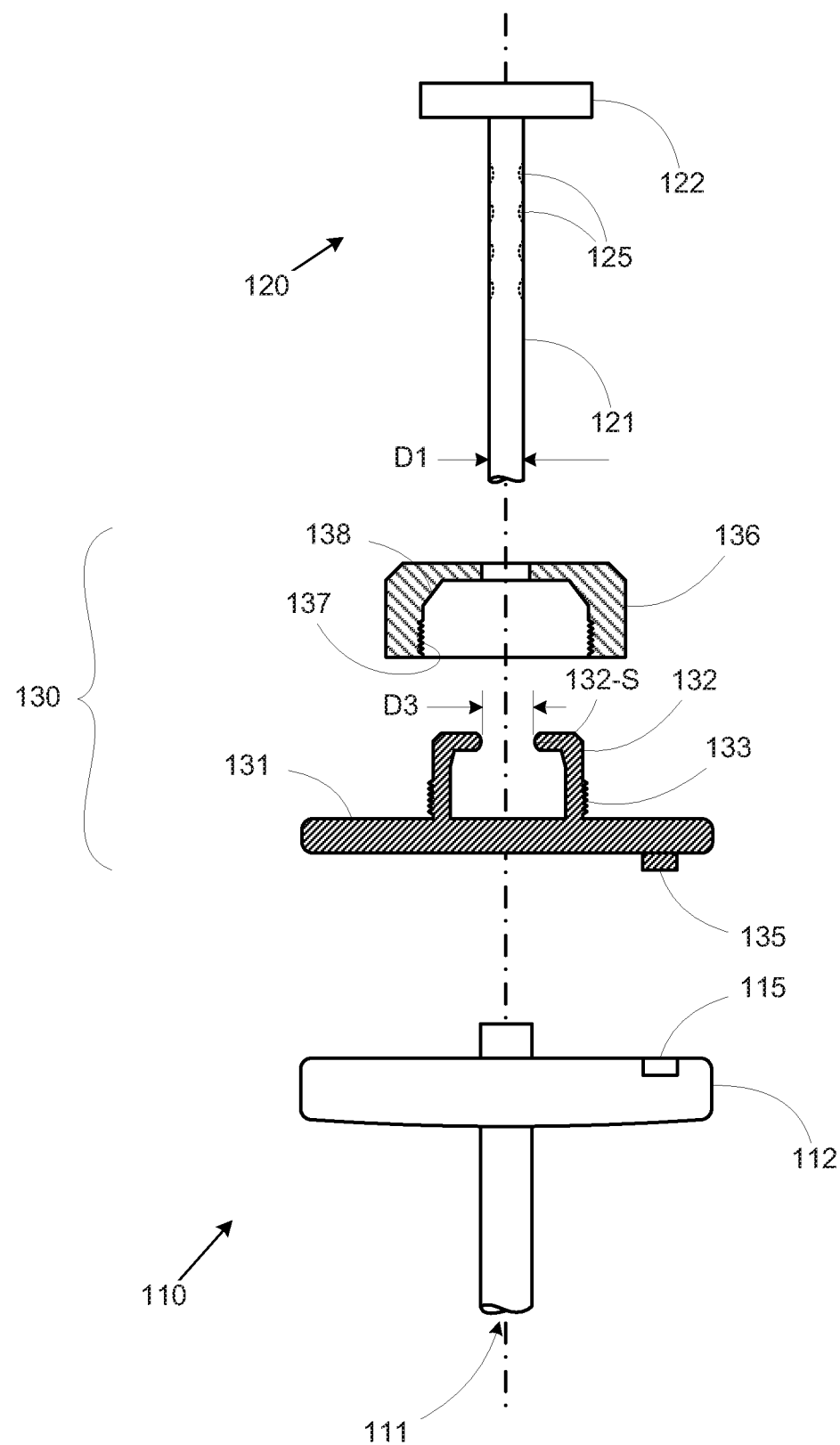

In various other embodiments, the gripping action provided by retainer 130 can be generated by a compression mechanism, such as shown in FIG. 4C. FIG. 4C shows another exemplary retainer 130 that is similar to the embodiment shown in FIGS. 4A and 4B, and includes a base structure 131 having (or coupled) to gripping elements 132 and a securing element 135. As described above with respect to FIGS. 4A and 4B, securing element 135 can be a latch, clip, pin, hook, snap, magnet, or any other mechanism that can secure retainer 130 to cannula 110 via a mating securing element 115.

Figure 4D:
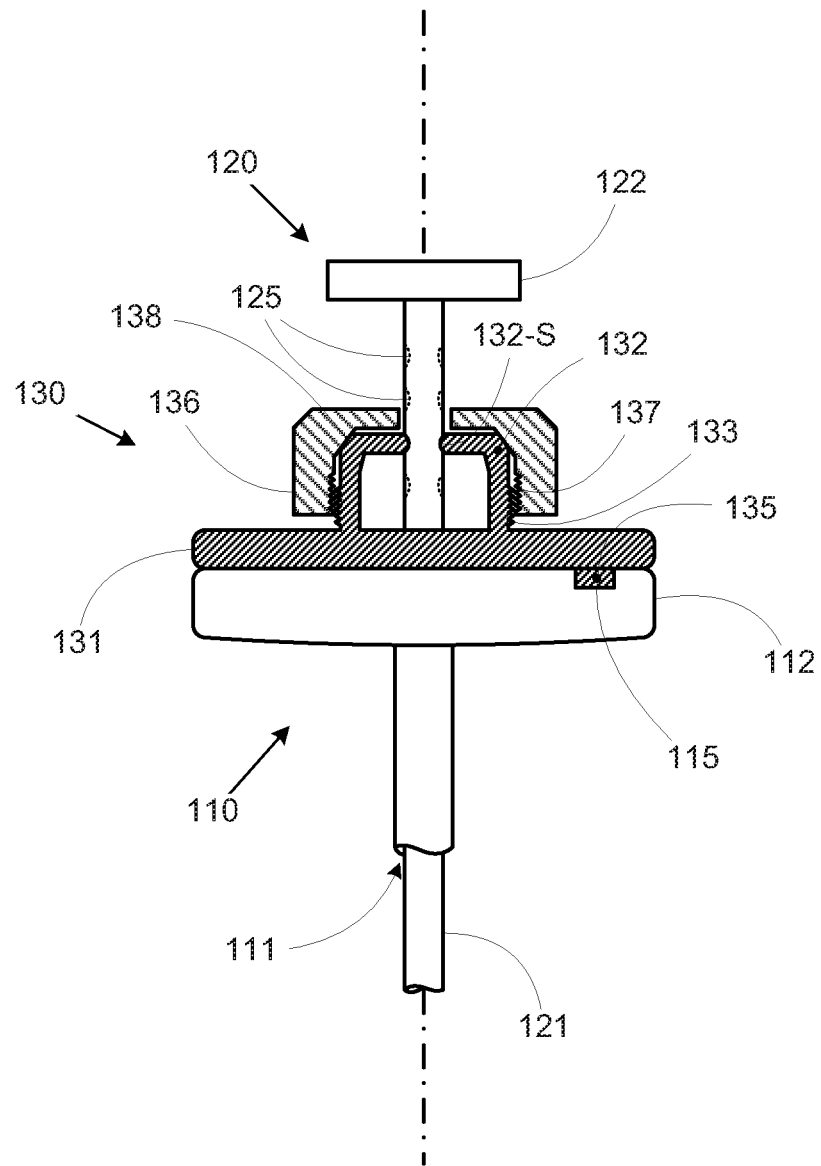

However, unlike the embodiment shown in FIGS. 4A and 4B, the gripping surfaces 132-S in retainer 130 of FIG. 4C have a default spacing distance D3 that is greater than dimension D1 of the gripping region of delivery nozzle 120. Therefore, retainer 130 also includes a cap 136 having internal threads 137 to mate with the threads 133 of gripping arms 132, and an internal taper 138. When cap 136 is screwed down on to gripping arms 132, as shown in FIG. 4D, internal taper 138 forces the gripping arms 132 inward, thereby clamping gripping surfaces 132-S onto delivery nozzle 120.

In some embodiments, gripping surfaces 132-S can mate with optional mating features 125 (e.g., detents, grooves, ridges, bumps, indentations, or features) on delivery nozzle 120 that provide distinct gripping locations for gripping surfaces 132-S.

In various other embodiments, the compressive loading provided by threaded cap 136 could be provided by a ratcheting mechanism, a spring-loaded mechanism, a cammed mechanism, or any other mechanism capable of selectively forcing gripping surfaces 132-S towards inward.

FIGS. 2B-2G show an exemplary use of retainer 130 in the performance of a minimally invasive surgical procedure. FIG. 2A shows a portion of a human vertebral column having vertebrae 201, 202, and 203. Vertebra 202 has collapsed due to a vertebral compression fracture (VCF) 202-F that could be the result of osteoporosis or cancer-related weakening of the bone. The abnormal curvature of the spine caused by VCF 202-F can lead to severe pain and further fracturing of adjacent vertebral bodies.

One treatment for this type of fracture is to perform a minimally invasive procedure in which a reinforcing bone filler material is injected into the fractured vertebra, either directly into the fractured region (vertebroplasty) or into a cavity created beforehand in the cancellous bone structure (kyphoplasty). Kyphoplasty is often a preferred technique due to the enhanced cement placement control provided versus vertebroplasty, along with the potential height restoration that can be achieved during the cavity creation phase of a kyphoplasty procedure.

Figure 2B:
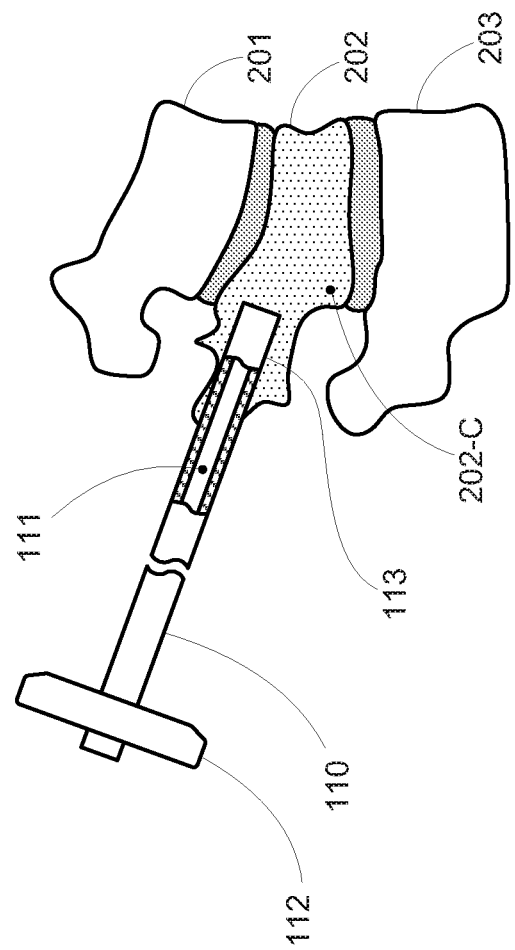
FIGS. 2A-2G show an exemplary use of the system of FIG. 1 to perform a surgical procedure.
Figure 2A:
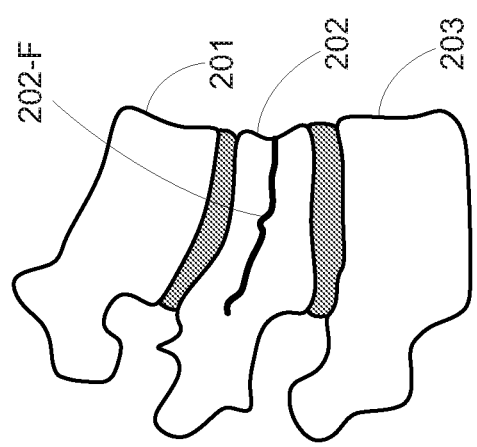

FIG. 2B shows a cannula 110 being positioned next to the target surgical location, which in this case is the cancellous bone structure within fractured vertebra 202. In this manner, a percutaneous path to vertebra 202 is provided via an interior lumen 111 of cannula 110. Typically, cannula 110 is docked into the exterior wall of the vertebral body (using either a transpedicular or extrapedicular approach) using a guide needle and/or dissector, after which a drill or other access tool (not shown) is used to create a path further into the cancellous bone 202-C of vertebra 202. However, any other method of cannula placement can be used to position cannula 110. Once docked, the distal end 113 of cannula 110 is substantially secured by the hard cortical (outer) bone of vertebra 202.

Figure 2C:
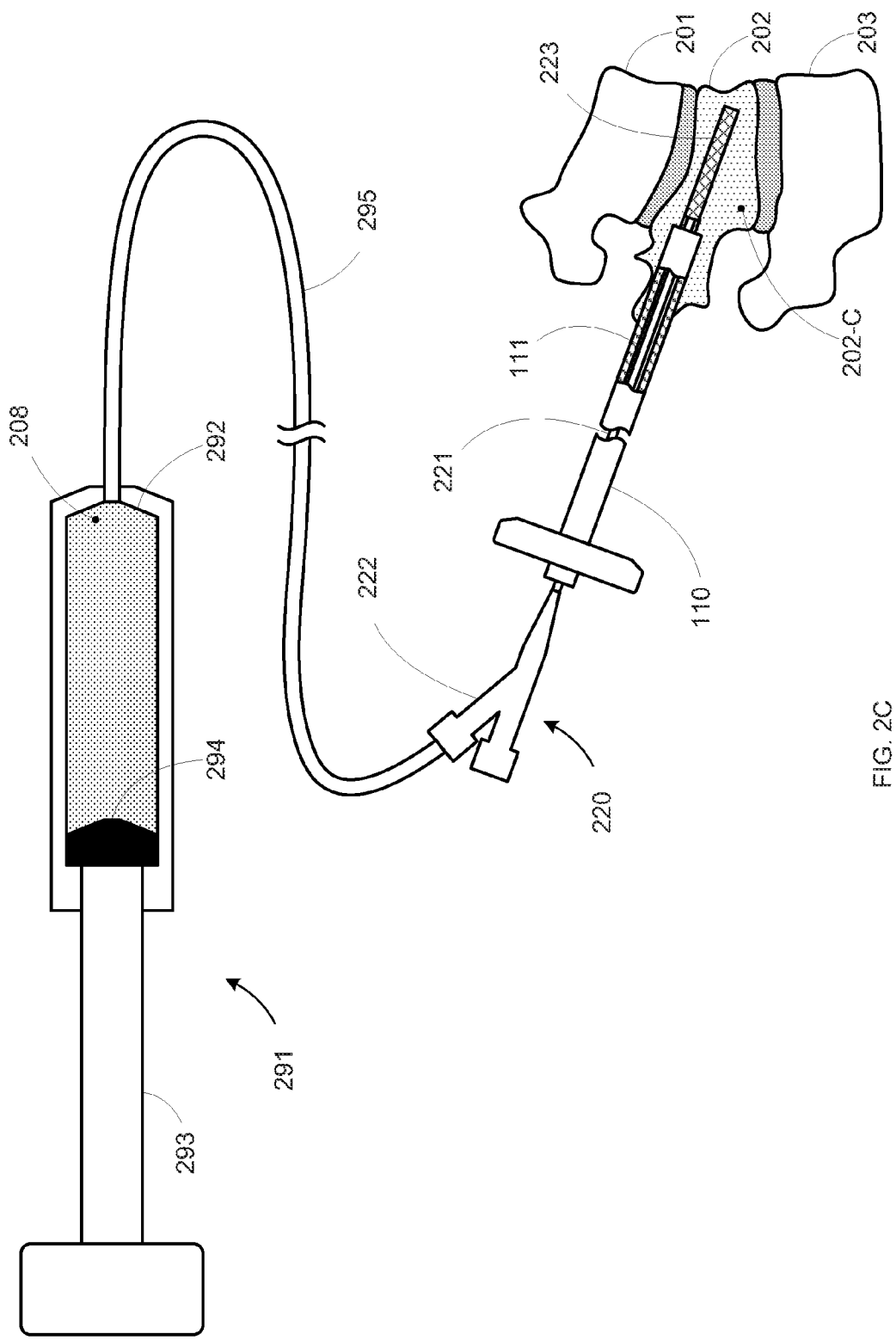

Then in FIG. 2C, an inflatable bone tamp 220 is placed into cannula 110. Inflatable bone tamp 220 includes a shaft 221 (e.g., a catheter), an expandable structure 223 (e.g., a balloon) at the distal end of shaft 221, and a connector 222 (e.g., a Luer Lock fitting) at the proximal end of shaft 221. Inflatable bone tamp 220 is coupled by flexible tubing 295 to an inflation syringe 291.

Figure 2D:
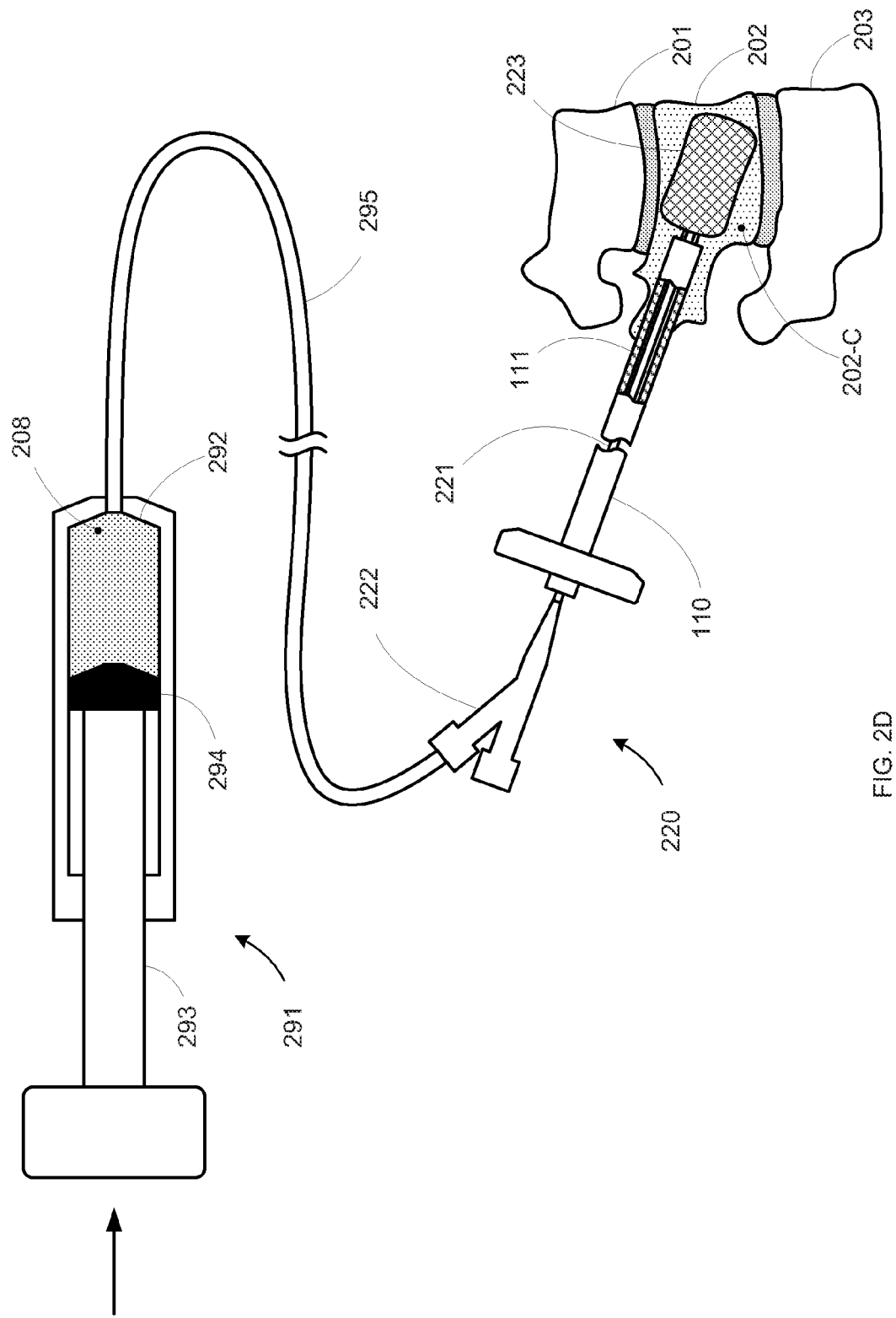

Syringe 291 includes a reservoir 292 and a plunger 293. Plunger 293 includes a plunger tip 294 that is slidably disposed in reservoir 292. To inflate expandable structure 223, a force is applied to plunger 291 that drives plunger tip 294 through reservoir 292, thereby expressing flowable material 209 through tubing 295, connector 222, and shaft 221, and into expandable structure 223. The resulting expansion of expandable structure 223 compresses the surrounding cancellous bone 202-C to create a well-defined cavity within fractured vertebra 202, and can also restore some or all of the original height of the vertebral body, as shown in FIG. 2D.

Figure 2E:
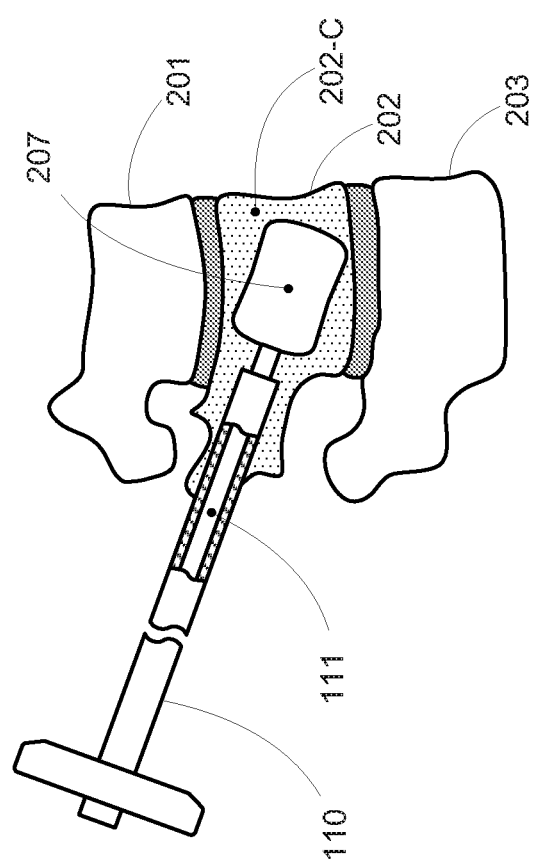
Figure 2F:
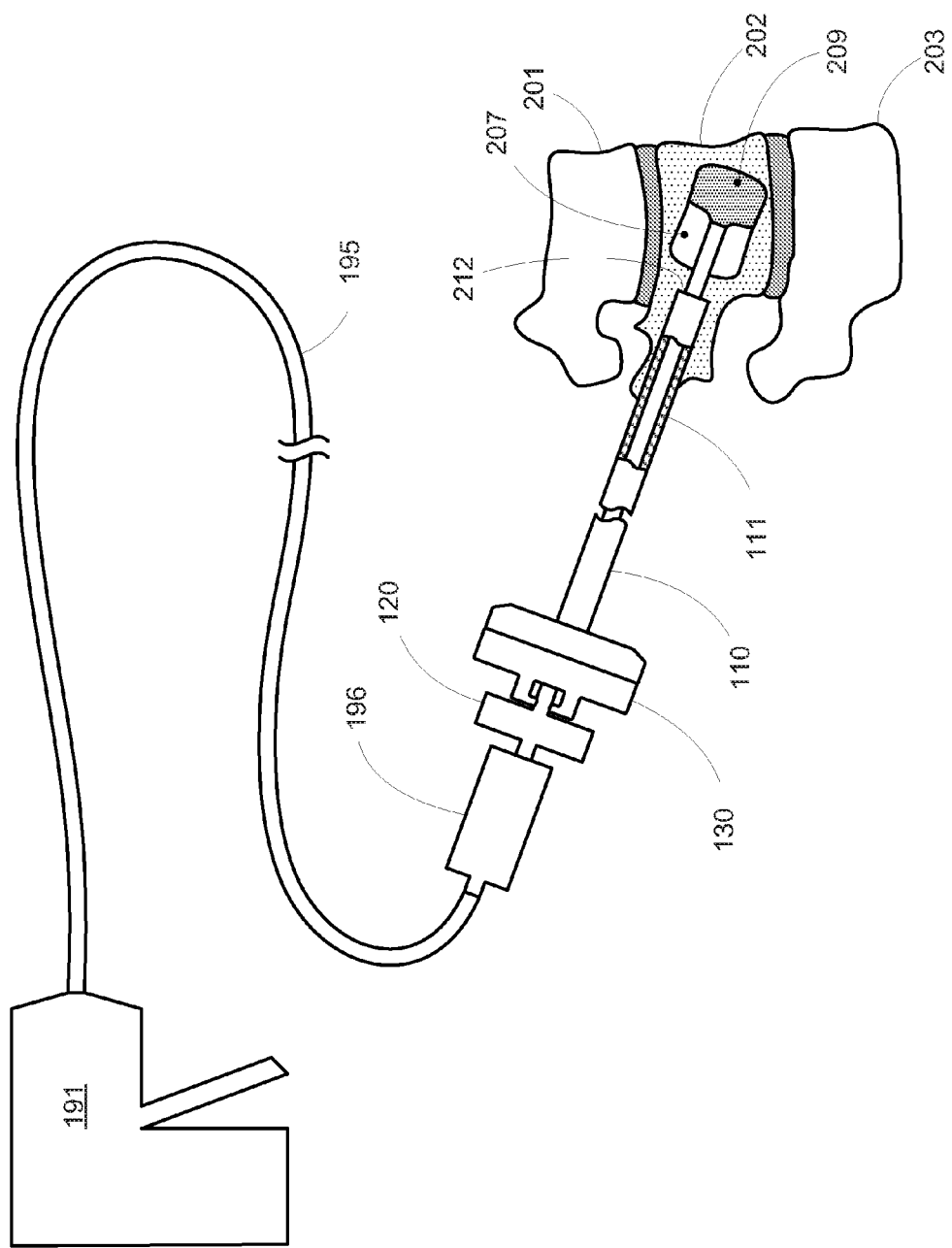

Once expandable structure 223 has been expanded to a desired volume, it is contracted and removed from vertebra 202 through cannula 110. As shown in FIG. 2E, the result of the previously described expansion procedure is a well-defined cavity 207 in cancellous bone 202-C. Cavity 207 can then be filled with bone filler material 209 (e.g., PMMA), as shown in FIG. 2F. A delivery nozzle 120 is inserted through cannula 110 and into cavity 207, and is fed bone filler material 209 from a cartridge 196 that it then directs into cavity 207. Cartridge 196 is coupled to a hydraulic actuator 191 by a hydraulic line 195 that drives bone filler material 209 from cartridge 196 using hydraulic pressure (e.g., by driving a piston inside cartridge 196 via the hydraulic pressure).

To prevent delivery nozzle 120 from moving or twisting within cannula 110 due to the loading from hydraulic line 195, a retainer 130 secures nozzle 120 to cannula 110. Retainer 130 can have any construction (e.g., as described with above with respect to FIGS. 1 and 4A-4D) that enables the securing of delivery nozzle 120 to cannula 110. Retainer 130 therefore allows the bone filler material delivery process to be performed consistently and reliably, even as high pressures generated within hydraulic line 195 increase the loading on delivery nozzle 120, and permits the physician to remain outside the fluoroscopic radiation field used to visualize the target site.

Figure 2G:
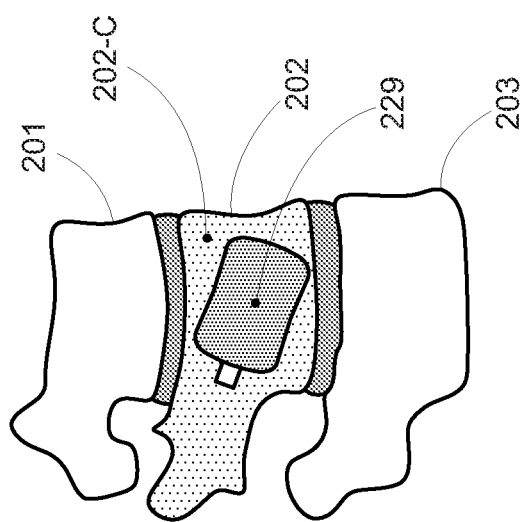

Once the filling operation is complete, delivery nozzle 120, retainer 130, and cannula 110 are removed from vertebra 202 as shown in FIG. 2G. Upon hardening, bone filler material 209 provides structural support for vertebra 202, thereby substantially restoring the structural integrity of the bone and the proper musculoskeletal alignment of the spine. In this manner, the pain and attendant side effects of a vertebral compression fracture can be addressed by a minimally invasive kyphoplasty procedure.

Note that the kyphoplasty procedure described with respect to FIGS. 2A-2G incorporates an inflatable bone tamp for cavity creation and a hydraulically-operated cement delivery system for explanatory purposes only. In various other embodiments, cavity creation can be performed using other types/combinations of mechanical systems (e.g., an expandable mechanism, a stent, a cutting tool, a coring tool, etc.), and bone filler delivery can be accomplished via other types of flow control mechanisms (e.g., a syringe coupled directly to the nozzle, a syringe coupled directly to the nozzle that is remotely controlled via a cable, a high pressure pumping system for pumping bone filler material from a remote location to the nozzle, etc.).

Figure 3:
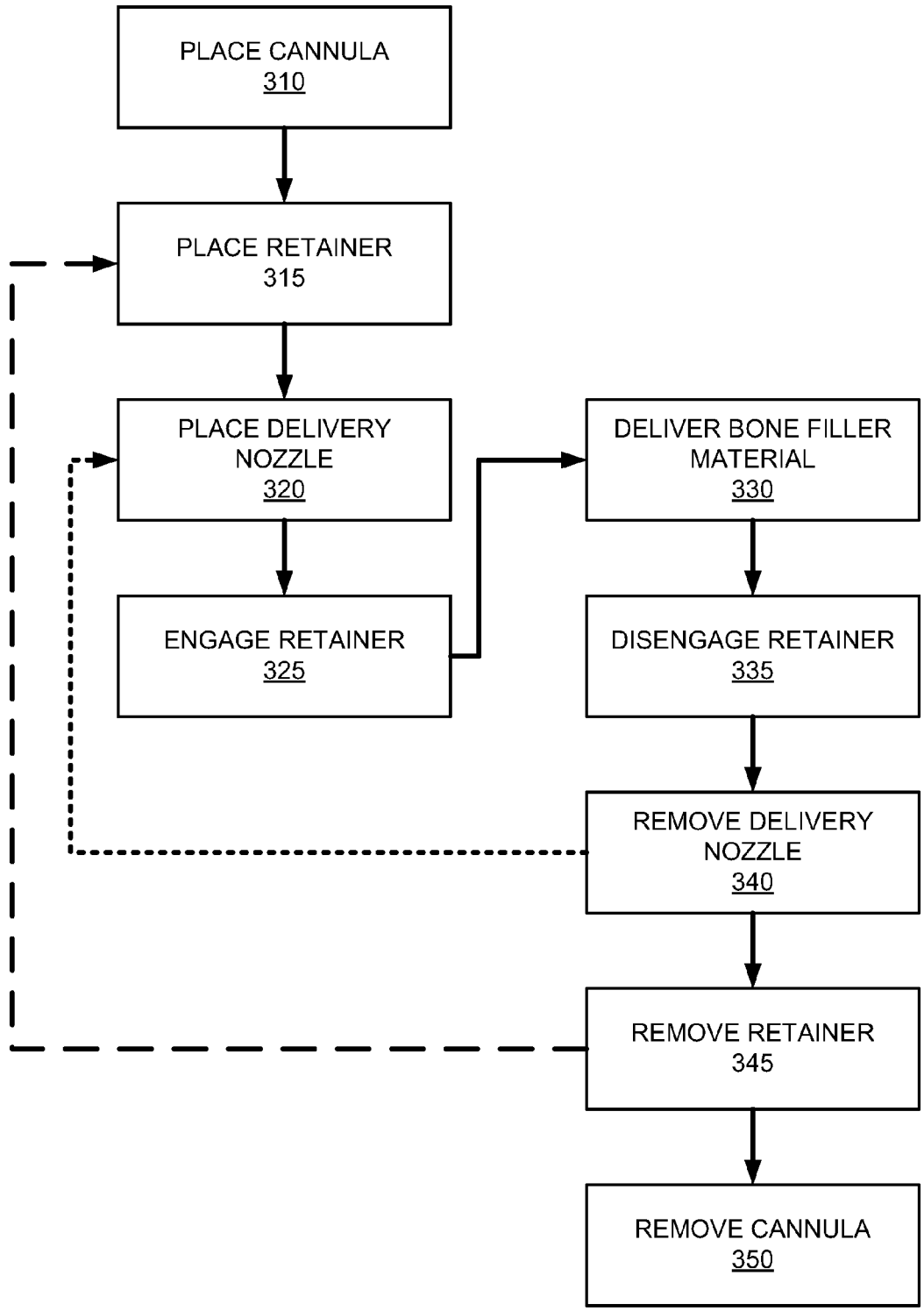
FIG. 3 is a flow diagram for a surgical procedure using the system of FIG. 1.

FIG. 3 shows a flow diagram of a process for performing a surgical procedure using a delivery nozzle and retainer as described with respect to FIGS. 1 and 2A-2G. In a PLACE CANNULA step 310, a cannula (e.g., cannula 110 shown in FIG. 2B) is docked next to a surgical target (e.g., docked into the cortical bone of a vertebra 202, as shown in FIG. 2B). As noted above, this placement operation can be performed using any necessary accessory tools, such as a needle, a guidewire, a drill, an obturator, or a mallet, among others.

Then, in a PLACE RETAINER step 315, a delivery nozzle retainer (e.g., retainer 130 shown in FIG. 2F) is affixed to the cannula (e.g., as described with respect to FIGS. 4A-4D using a latch, clip, pin, hook, snap, magnet, or any other securing mechanism). A bone filler material delivery nozzle (e.g., delivery nozzle 120 as described with respect to FIG. 2F) is then inserted into the cannula in a PLACE DELIVERY NOZZLE step 320. Note that in various embodiments, the retainer could be preassembled with either the cannula or delivery nozzle, in which case step 315 can be eliminated.

Note that any number of additional procedure steps can be performed between the placement of the cannula in step 310 and the steps 315 and/or 320. For example, as described above with respect to FIGS. 2C-2E, a cavity could be formed in a vertebral body prior to the delivery nozzle being placed into the vertebral body.

Next, in an ENGAGE RETAINER step 325, the delivery nozzle retainer is engaged with the delivery nozzle to establish a fixed position for the delivery nozzle with respect to the cannula (e.g., as described with respect to FIGS. 2C, 2F, and 4A-4D). Note that in some embodiments, the retainer can be engaged with the delivery nozzle continuously once the delivery nozzle is placed within the retainer (i.e., the delivery nozzle is held securely but not fixedly (i.e., sufficient force can cause movement), such as described with respect to FIGS. 4A-4B). In various other embodiments, the retainer can be engaged with the delivery nozzle once the desired positioning of the delivery nozzle has been established (i.e., the delivery nozzle moves freely in the cannula until the retainer is actuated, such as described with respect to FIGS. 4C-4D).

A minimally invasive surgical procedure (e.g., cavity creation within bone, such as described with respect to FIG. 2D, or bone filler material delivery within bone, such as described with respect to FIG. 2F) is then performed using the delivery nozzle in a DELIVER BONE FILLER MATERIAL step 330. In one embodiment, step 330 can involve dispensing the material through the delivery nozzle remotely via a flexible coupling (e.g., delivering cement to a target location using a remotely actuated hydraulic pumping system coupled to a cement cartridge/delivery nozzle via a hydraulic line as described with respect to FIG. 2F).

Upon completion of the bone filler material delivery, the retainer can be disengaged from the delivery nozzle in a DISENGAGE RETAINER step 335, and the delivery nozzle removed from the cannula in a REMOVE DELIVERY NOZZLE step 340. Note that in various embodiments, steps 335 and 340 can be performed substantially simultaneously (e.g., if the retainer applies a continuous gripping force to the delivery nozzle).

The retainer can be removed in a REMOVE RETAINER step 345, and the cannula can be removed in a REMOVE CANNULA step 350 to complete the surgical procedure. Note once again that various additional procedure steps can be performed between steps 345 and 350. Note further that in various embodiments, multiple different bone filler material delivery operations can be performed through the same cannula (e.g., delivering a first quantity of material, and then delivering a second quantity of the same or different material), in which case, after step 345, the process could return to steps 315, as indicated by the dashed line. Note that in various other embodiments, the same retainer could be used for multiple delivery nozzles, in which case, after step 340, the process could return to step 320, as indicated by the dotted line. Various other sequences of steps will be readily apparent.

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain steps may be performed concurrently in a parallel process when possible, as well as performed sequentially as described above. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

The invention claimed is:

1. A system comprising:
   a cannula comprising an interior lumen;
   a bone filler material delivery nozzle comprising a proximal end having a handle and an opposite distal end, the distal end being positioned within the interior lumen, the bone filler material delivery nozzle being configured for conveying bone filler material to a target location through the interior lumen;
   a retainer comprising gripping arms for coupling the bone filler material delivery nozzle to a proximal end of the cannula to prevent movement of the bone filler material delivery nozzle relative to the cannula, the retainer being spaced apart from the interior lumen; and
   a clamping element positioned between the retainer and the handle when in an assembled configuration,
   wherein the bone filler material delivery nozzle has a gripping region having a first dimension, gripping surfaces of the gripping arms having a default spacing of a second dimension, the second dimension being greater than the first dimension, the clamping element being configured to engage the retainer to move the gripping arms inward such that the gripping surfaces engage the gripping region.

2. The system of claim 1, wherein the gripping arms are flexible.

3. The system of claim 1, wherein the gripping surfaces comprise one or more resilient elements mounted on the gripping arms.

4. The system of claim 1, wherein the clamping element comprises an inner thread that engages outer threads of the gripping arms, the inner thread engaging the outer threads such that rotation of the clamping element relative to the retainer moves the clamping element axially relative to the retainer to force the gripping arms inward such that the gripping surfaces engage the gripping region.

5. The system of claim 4, wherein the clamping element comprises an internal taper for forcing the gripping arms inward as the clamping element moves axially relative to the retainer.

6. The system of claim 4, wherein the gripping region comprises a plurality of spaced apart detents, the gripping surfaces being configured for disposal in two of the detents when the clamping element forces the gripping arms inward to fix the retainer relative to the bone filler material delivery nozzle.

7. The system of claim 1, wherein the bone filler material delivery nozzle comprises a first positioning feature for positively mating with at least one of the gripping arms to position the bone filler material delivery nozzle at a first position relative to the cannula.

8. The system of claim 7, wherein the bone filler material delivery nozzle comprises a second positioning feature for positively mating with the at least one of the gripping arms to position the bone filler material delivery nozzle at a second position relative to the cannula.

9. The system of claim 1, wherein the retainer is integrated with the cannula.

10. The system of claim 1, wherein the gripping arms are rigid and the gripping surfaces each comprise a resilient element selected from a group consisting of an elastomer, an o-ring, a gasket and a spring-loaded tip.

11. The system of claim 1, wherein the gripping region comprises a plurality of spaced apart detents, the gripping surfaces being configured for disposal in two of the detents to fix the retainer relative to the bone filler material delivery nozzle.

12. The system of claim 1, wherein:
the retainer comprises a base structure comprising a proximal surface and a distal surface opposite the proximal surface, the gripping arms extending from the proximal surface, the distal surface comprising a projection extending threrefrom; and
the cannula comprises a proximal surface having a blind hole therein, the projection being disposed in the blind hole to secure the retainer to the cannula.

13. The system of claim 1, wherein:
outer surfaces of each of the gripping arms comprise a first thread form;
an inner surface of the clamping element comprises a second thread form that engages the first thread form; and
a base structure of the retainer comprises a first opening and the clamping element comprises a second opening that is coaxial with the first opening, the bone filler material delivery nozzle extending through each of the first and second openings.

14. The system of claim 13, wherein:
the gripping arms each include a vertical portion extending from the base structure and a horizontal portion extending from the vertical portion, ends of the horizontal portions defining the gripping surfaces, interfaces between the vertical and horizontal portions each defining a tapered portion that extends at an acute angle relative to the vertical portions; and
the clamping element comprises an internal taper that engages the interfaces to force the gripping arms inward.

15. The system of claim 13, wherein rotating the clamping element relative to the base structure forces the gripping arms inward.

16. The system of claim 1, wherein the retainer is movable from a first configuration in which the gripping surfaces are spaced apart from the gripping region to a second configuration in which the gripping surfaces engage the gripping region.

17. A system comprising:
a cannula comprising an interior lumen;
a bone filler material delivery nozzle comprising a proximal end having a handle and an opposite distal end, the distal end being positioned within the interior lumen, the bone filler material delivery nozzle being configured for conveying bone filler material to a target location through the interior lumen;
a retainer comprising gripping arms for coupling the bone filler material delivery nozzle to the cannula to prevent movement of the bone filler material delivery nozzle relative to the cannula; and
a clamping element positioned between the retainer and the handle when in an assembled configuration, the clamping element being configured to engage the retainer to move the retainer from a first configuration in which gripping surfaces of the gripping arms are spaced apart from a gripping portion of the bone filler material delivery nozzle to a second configuration in which the gripping surfaces engage the gripping portion.

18. The system of claim 17, wherein a proximal end of the cannula extends through an opening in the retainer.

19. A system comprising:
a cannula comprising an interior lumen;
a bone filler material delivery nozzle comprising a proximal end having a handle and an opposite distal end, the distal end being positioned within the interior lumen, the bone filler material delivery nozzle being configured for conveying bone filler material to a target location through the interior lumen;
a retainer comprising gripping arms extending from a threaded base of the retainer, the gripping arms being configured for coupling the bone filler material delivery nozzle to the cannula to prevent movement of the bone filler material delivery nozzle relative to the cannula; and
a clamping element configured to engage the retainer to force the gripping arms inward such that the gripping surfaces engage a gripping portion of the bone filler material delivery nozzle, the clamping element comprising threads for mating with the threaded base and an internal taper for forcing the gripping arms inward as the threads mate with the threaded base, the clamping element being positioned between the retainer and the handle of the bone filler material delivery nozzle when in an assembled configuration.

* * * * *

UNITED STATES PATENT AND TRADEMARK OFFICE
CERTIFICATE OF CORRECTION

| | |
|---|---|
| PATENT NO. | : 9,545,281 B2 |
| APPLICATION NO. | : 14/316299 |
| DATED | : January 17, 2017 |
| INVENTOR(S) | : Donovan et al. |

Page 1 of 1

It is certified that error appears in the above-identified patent and that said Letters Patent is hereby corrected as shown below:

In the Specification

In Column 1, Line 8, delete "2009," and insert -- 2009, now Pat. No. 8,821,505, --, therefor.

In Column 5, Line 52, delete "FIGS. 2B-2G" and insert -- FIGS. 2A-2G --, therefor.

In Column 6, Line 28, delete "plunger 291" and insert -- plunger 293 --, therefor.

In Column 6, Line 55, delete "with above" and insert -- above --, therefor.

Signed and Sealed this
Eleventh Day of April, 2017

Michelle K. Lee
*Director of the United States Patent and Trademark Office*